(12) United States Patent
Wharton (10) Patent No.: US 9,474,444 B2
(45) Date of Patent: Oct. 25, 2016

(54) METHOD AND APPARATUS FOR SELF-EXAMINATION OF THE INTERIOR SPACE OF AN INDIVIDUAL'S EYE

(71) Applicant: GROUP SIBISCOPE, LLC, Las Vegas, NV (US)

(72) Inventor: Michael Wharton, Las Vegas, NV (US)

(*) Notice: Subject to any disclaimer, the term of this patent is extended or adjusted under 35 U.S.C. 154(b) by 92 days.

(21) Appl. No.: 14/614,750

(22) Filed: Feb. 5, 2015

(65) Prior Publication Data
US 2015/0230703 A1    Aug. 20, 2015

Related U.S. Application Data

(60) Provisional application No. 61/941,914, filed on Feb. 19, 2014.

(51) Int. Cl.

| | | |
|---|---|---|
| *A61B 3/13* | (2006.01) | |
| *A61B 3/00* | (2006.01) | |
| *G02B 26/08* | (2006.01) | |
| *G02B 27/02* | (2006.01) | |
| *A61B 3/12* | (2006.01) | |

(52) U.S. Cl.
CPC ............. *A61B 3/13* (2013.01); *A61B 3/0008* (2013.01); *A61B 3/12* (2013.01); *G02B 26/0816* (2013.01); *G02B 27/024* (2013.01)

(58) Field of Classification Search
CPC ............ G02B 26/0816; G02B 27/024; G02B 27/025; G02B 7/02; A61B 3/13; A61B 3/0008; A61B 3/12; A61B 3/14; A61B 3/02; A61B 3/125; A61B 3/10; A61B 3/1208; A61B 3/107
USPC ................................. 351/206, 221
See application file for complete search history.

(56) References Cited

U.S. PATENT DOCUMENTS

| | | | |
|---|---|---|---|
| 4,682,867 A | | 7/1987 | Gould |
| 4,750,831 A | * | 6/1988 | Vega ............ A61B 3/107 351/223 |
| 5,801,807 A | | 9/1998 | Satake |
| 6,144,508 A | | 11/2000 | Bransome |
| 2002/0047992 A1 | | 4/2002 | Graves |
| 2009/0096988 A1 | | 4/2009 | Fink |
| 2011/0170068 A1 | | 7/2011 | Dan-Gur |
| 2011/0299036 A1 | | 12/2011 | Goldenholz |
| 2012/0050683 A1 | | 3/2012 | Yates |

OTHER PUBLICATIONS

EyeView Visualizing Scope; Richmond Products Eye Examination and Testing Products catalog, p. 107.
FloatScope, Opticom Data Research.
PCT Search Report from corresponding PCT application, PCT/US2015/015138, dated May 22, 2015.
PCT Written Opinion from corresponding PCT application, PCT/US2015/015138, dated May 22, 2015.

* cited by examiner

*Primary Examiner* — Euncha Cherry
(74) *Attorney, Agent, or Firm* — Stine Law Ltd (57) ABSTRACT

A method and apparatus for self-examination of the interior space of an individual's eye is disclosed.

21 Claims, 11 Drawing Sheets

METHOD AND APPARATUS FOR SELF-EXAMINATION OF THE INTERIOR SPACE OF AN INDIVIDUAL'S EYE

BACKGROUND

An individual's vision may be diminished over time by a variety of microscopic-sized particles which accumulate in the clear and transparent aqueous jelly inside the area of the individual's eye known as the vitreous humor. These particles might be noticed as blurry, opaque areas in an individual's field of view, which might make it hard for one to focus on whatever is being looked at. Or sometimes the individual might see various partially and vaguely outlined particles of differing sizes and shapes which may be referred to as 'floaters', 'blurs', 'spots', 'webs', or 'threads.' Such particles may be detected, but only briefly observed, by looking up at a cloudless blue sky, and then while turning to face away from the sun, an individual may notice the particles that suddenly and briefly 'float' into the field of view and then just as suddenly may disappear.

Again these particles are not in the air, but rather inside an individual's eye. And since they are situated in the eye, they can become a health problem by obstructing or blurring an individual's vision, thus making it hard to focus on anything being looked at. The problem may worsen with age.

In accordance with my present invention, my method and apparatus enables the individual to continually observe, in sharp focus, such particles as if seen through a microscope, such as at an approximately 200× magnification in their natural and original position ('in situ'). Doing so, the individual may discern such particles well enough to identify and categorize the same as either residual pieces of organic detritus matter, or as growths of invasive microorganisms, which accumulate over time. By using helpful visual aids such as conventional microscope photos, drawings, or other graphic media of microorganisms known to be invasive of humans, the individual may be able to categorize some of the observed particles as invasive microorganism growths, and with such knowledge, he/she is better prepared to monitor and address related health symptoms of such invasive microorganisms. This may result in additional health benefits in addition to improving one's vision.

The method and apparatus permits an individual to self-examine the particles within the eye, behind his/her lens. The apparatus does not allow an individual to examine another person's eye such as a health care professional examining a patient's eye.

One example of invasive and pathogenic microorganisms, the fungus/yeast *Candida*, may be observed when using the apparatus if the yeast has invaded the inner eye. However before proceeding with this specific example of *Candida*, it will be understood that other microbiological genus and species may be detected and observed if and when they likewise invade the vitreous humor area of the eye. Therefore using this method and apparatus to study other genus and species of invasive microbes is fully within the purpose, intent, spirit and scope of my invention. Additionally a wide variety of microscopic-sized pieces of organic detritus matter may also accumulate over time and be observed within the individual's eye and which may cause vision blurs, shadows, floaters, etc. These also can be studied with the method and apparatus and are likewise included within the purpose, intent, spirit and scope of my invention. My invention is not limited to the detection, observation and studying of the *Candida* yeast only.

Continuing with the *Candida* example, it may be helpful to know that this particular microorganism has an ability to transform from a commensal microbe (one that obtains food or other benefit from the human body without damaging it) to an invasive and often opportunistic pathogen by transforming to a twisted, thread-like filamentous form referred to as 'hyphae' or the 'hyphal' form. Therefore if an individual had the ability or means to see and detect the hyphal form as it invades the eye, the individual could then be on alert for other associated health risks and symptoms related to an infection of this fungus/yeast including, but not limited to, oral thrush, athlete's foot, ringworm, vaginitis and candidiasis. As is known, the presence of such microorganisms may cause serious health conditions in a human. Noticing and detecting these other symptoms could confirm the presence of this invasive pathogen as seen with the apparatus, and thus alert the individual to action and to seek medical help to control or eradicate the infection.

Presently one of the quickest and most reliable ways to diagnose the invasive hyphal form of *Candida* is by microscopic examination. See FIG. 13. However there are some disadvantages and problems with microscopic examination such as the time and expense to prepare a specimen before it can be placed on a glass slide under the microscope. First a suitable specimen must be obtained from a source considered likely to harbor the pathogen. If obtaining the specimen requires surgery, extra time and expense may incur. Second the collected specimen requires laboratory preparation such as fixation, tissue processing, embedding, sectioning and staining before it can be placed on a glass slide under the microscope, thus more time and expense.

By using this apparatus to detect the invasive fungus/yeast as it grows inside the eye, an individual may save the time and expense of exploratory surgery and/or biopsy, and lab preparation of the specimen for microscopic examination by allowing the individual to instantly view and detect the presence of the hyphal form of *Candida* if it has indeed invaded the eye. So the usual process of microscopic analysis which may take hours or days, all the while accruing fees and expenses, can instead be done instantly by self-examination in the comfort and convenience of the individual's own choosing not needing to travel to a doctor's office, clinic, or medical laboratory, and without any lab fees. Because the apparatus is for self-examination, and because the clear and transparent gel of the vitreous humor is naturally an ideal media for light-illuminated viewing, the invasive pathogen can be instantly detected 'in situ' with the apparatus if it has actually invaded the interior of the eye.

One potential disadvantage of the device for an inexperienced layman is not knowing how to identify or distinguish the hyphal form of *Candida* from any other particles seen inside the eye. The layman may not understand the significance of what is seen 'in situ' with the apparatus.

Fortunately one relatively easy way for the layman to learn how to recognize and identify the invasive hyphal form of *Candida* is the same method by which experienced medical lab personnel have learned: by holding in the one hand microscope photos of *Candida* with identifying features noted and annotated, and holding the microscope with specimen in the other hand. Knowledge is acquired by observing, comparing and matching such identifying features as the twisted, thread-like filamentous hyphal form, the germ tubes, the blastospores, and chlamydospores, etc. The only difference of the two methods is that when using the apparatus, the individual observes the specimen 'in situ' within his/her own eye instead of 'in vitro' on a glass slide under the microscope. Only the instrument used for observation has changed. The anatomically identifying features of *Candida* remain the same. Therefore to help the inexperienced individual recognize and identify *Candida* in the invasive form, several microscope photos of *Candida* at an approximately 200× magnification with annotations identifying the anatomical features may be provided with the apparatus.

Figure 1:
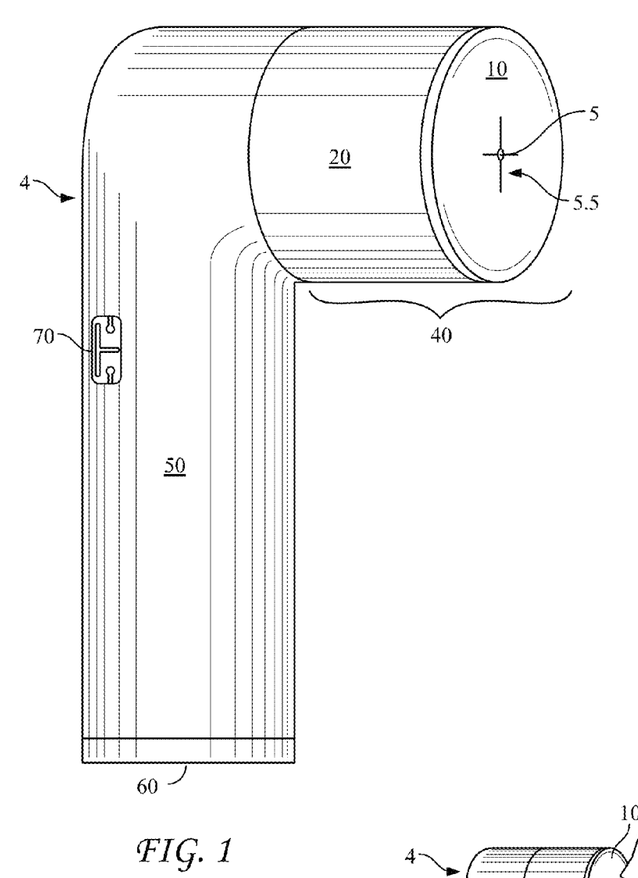
FIG. 1 is a perspective view of a first embodiment of an apparatus according to the present invention.
Figure 2:
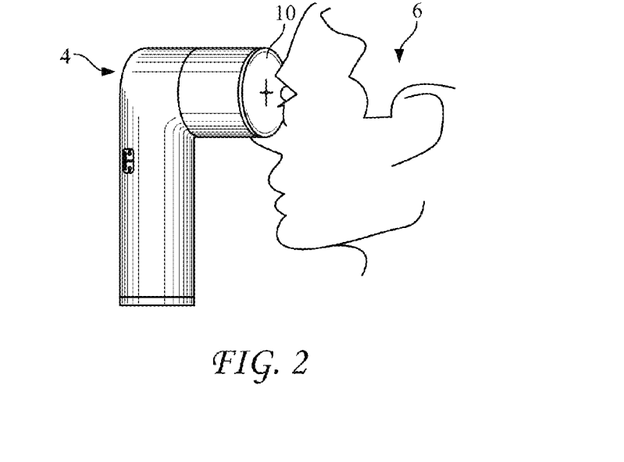
FIG. 2 is a perspective view of the apparatus of FIG. 1 in use by an individual.
Figure 3:
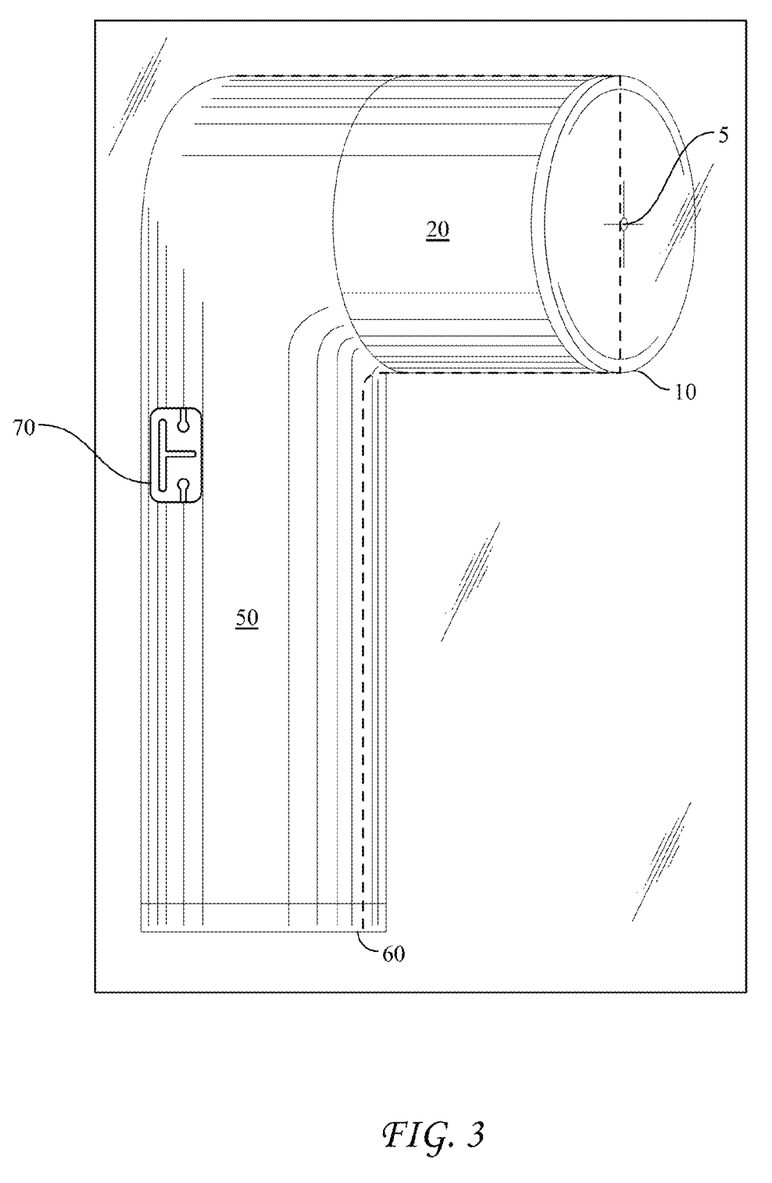
FIG. 3 is a further perspective view of the apparatus of FIG. 1.
Figure 8:
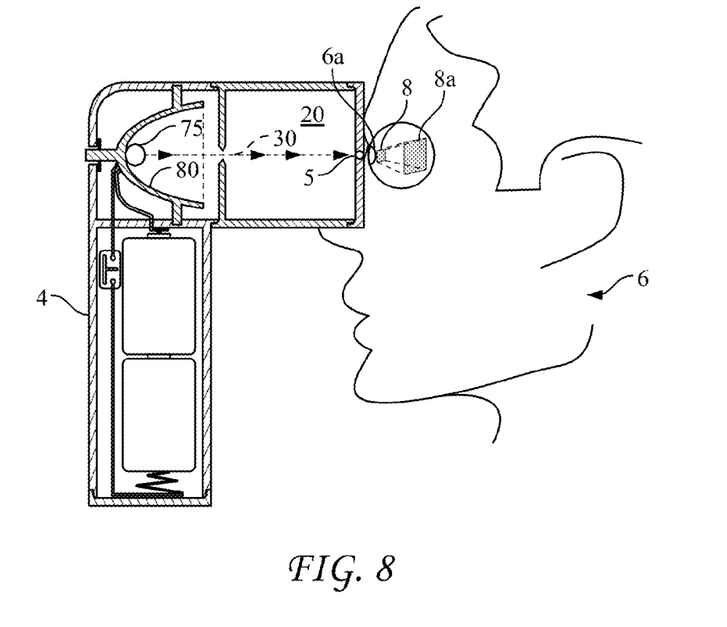
FIG. 8 is an illustration indicating perception of a particle with the apparatus of FIG. 1, illustrating a path of light from a light source to an eye.

Normal vision is accomplished by focusing on external samples which are external of the eye. By using the apparatus as indicated in FIG. 2, and FIG. 8, one's eye may focus internally. My apparatus provides 'self-viewing' or visual introspection of the vitreous particles inside an individual's own eye.

This apparatus utilizes and applies certain non-obvious properties of existing common optical components to allow the individual to visually identify the microscopic details of vitreous particles within the eye, behind the lens, in situ. The focusing and magnifying capabilities of this apparatus are the result of the combined light refracting properties of two lenses: the first lens is the lens of the individual's own eye (the human lens); and the second lens is the lens of my apparatus.

The human lens can greatly magnify these vitreous particles perceived size, but is less effective at focusing within the eye, behind the lens, which is where the vitreous particles accumulate. Thus the varied 'in situ' vitreous particles are perceived as opaque blurry areas, or vaguely outlined particles of various shapes and sizes which seem to briefly appear and float about, and then suddenly disappear. Thus it is the cumulative light refracting properties of both lenses, the human lens and the apparatus's lens, which allow the individual to continuously observe the particle in sharp focus and magnified to an approximately 200× original size.

Figure 7:
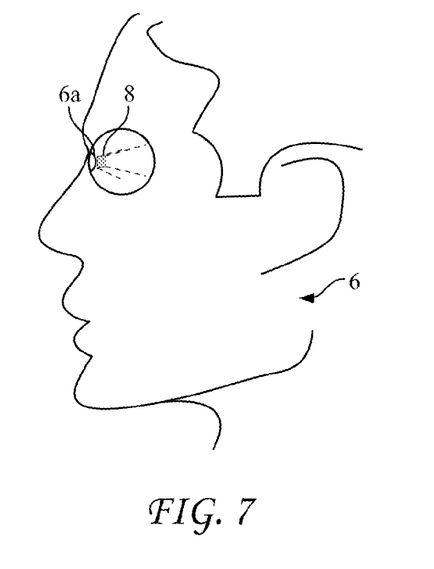
FIG. 7 is an illustration indicating perception of a particle with a naked eye.

For this reason, as indicated in FIG. 7, particles are perceived by the naked eye as out-of-focus, opaque, blurry areas, or as vaguely outlined particles which seem to briefly appear and float about, then suddenly disappear. When using the apparatus to view particles as indicated in FIG. 8, the particles are perceived in sharp focus because of the combined light refracting properties of both lenses—the human lens and the apparatus's lens—which allow the individual to continuously observe particles in situ.

Generally younger individuals will not observe particles as readily as older persons due to the longer time needed for 'particles' to accumulate within the eye.

SUMMARY

It is an object of the invention to provide an apparatus for self-examination of the interior space of an individual's eye.

In accordance with this aspect of my invention, the apparatus may comprise a lens mounted in the wall of a chamber, which may be substantially opaque. The chamber may have an aperture hole and a light source.

The lens may be a ball ("spherical") lens, a half-ball ("hemispherical") lens, or the like. The diameter of the lens may be in the range of 1 mm and 10 mm. The chamber may be divided into detachable subcomponents. The aperture hole may be in the range of 1 mm and 50 mm. The light source may be unattached or attachable. The light may originate from outside the aperture-portion of the chamber, and then radiate through the aperture hole, into the chamber, and then towards the lens. The attachable light source may be a conventional flashlight having a conventional light source, such as an incandescent light bulb, an LED light or array, or the like, situated within a reflector. The reflector may be manually deflected about its longitudinal axis by manipulating a tabbed appendage coupled to the reflector.

It is a further object of my invention to provide a method to permit one to utilize my apparatus to self-examine the interior space of an individual's eye.

In accordance with the method, the apparatus may be utilized by an individual to examine the interior space of the individual's eye by turning on the light source, and holding the lens spaced from the eye, in the range of 1/16" and 1". The individual then looks through the lens toward the light source, and examines the illuminated interior of the individual's eye while manipulating the tabbed appendage to deflect the reflector and thereby change the background lighting and contrast lighting of the interior of the individual's eye.

It is a further object of my invention to provide a method for self-examining the interior of an individual's eye comprising positioning an apparatus near a light source, such as flashlight-type light source, positioning a lens of the apparatus close to the individual's eye, looking through the lens toward the light source and self-examining the illuminated interior within the eye. The apparatus may comprise a lens mounted in the wall of a chamber, such as a substantially opaque chamber, which has an aperture hole and uses a source of visible light.

It is a further object of my invention to provide a method of self-examination for a presence of microorganisms, in situ, within an individual's eye. The method may comprise positioning an apparatus near a light source or attaching and turning on an attachable flashlight light source; positioning a lens of the apparatus close to the individual's eye; looking through the lens toward the light source; and self-examining the illuminated interior within the individual's eye for the presence of microorganisms in situ.

It is a further object to provide a method of self-examination for a presence of particles, or vision anomalies, also known as 'floaters,' in situ, which may accumulate within an individual's eye. The method may comprise positioning an apparatus near a light source or attaching and turning on an attachable flashlight light source, positioning a lens of the apparatus close to the individual's eye, looking through the lens toward the light source and self-examining the illuminated interior within the individual's eye for the presence of vision anomalies, in situ.

It is a further object to provide a system for self-examining for a presence of microorganisms, in situ, within an individual's eye. The system may comprise positioning an apparatus near a light source or attaching and turning on an attachable flashlight light source, positioning a lens of the apparatus close to an individual's eye, looking through the lens toward the light source and self-examining the illuminated interior within the individual's eye. The apparatus may comprise a lens mounted in the wall of an opaque chamber. The chamber may have an aperture hole, and the apparatus may use a source of visible light.

The lens may be in the shape of a ball (a 'spherical' lens), a half-ball ('hemispherical lens), or such other appropriate shape. The lens may be formed of any conventional lens material. The diameter of the lens may be in the range of 1 mm and 10 mm. However it has been found that one may vary the relative diameters of the aperture and the lens and obtain acceptable results. The chamber may be divided into detachable subcomponents. The aperture hole may be in the range of 1 mm and 30 mm. The light source may be unattached or attachable. The light may originate from outside the aperture-portion of the chamber and then radiate through the aperture hole, into the chamber, and then towards the lens.

The attachable light source may be a conventional flashlight having a bulb or LED. The light source may be situated in a reflector inside the flashlight. The reflector may be movable by manipulating a tabbed appendage of the reflector so that the individual can adjust background lighting and contrast lighting of the interior of the eye. One may desire to adjust the reflectivity of the reflector, such as depending on the strength of the light source. The reflectivity of the reflector may be adjusted by conventional means, such as by darkening all, or portions of, the reflector.

The system may be utilized by attaching, and turning on, the attachable flashlight light source, and holding the lens between one-sixteenth inch and one inch from the eye. The individual may look through the lens toward the source of light to examine the interior of the eye, and may use the tabbed appendage to adjust background and contrast lighting for what is seen.

DETAILED DESCRIPTION OF THE INVENTION

While my invention is susceptible to embodiment in many different forms, there will be described herein in detail, specific embodiments thereof with the understanding that the present disclosure is to be considered as an exemplification of the principles of the invention and is not intended to limit the invention to the specific embodiments illustrated.

A first embodiment of an apparatus, generally designated 4, in accordance with the present invention, is illustrated in FIGS. 1-8. The apparatus 4 comprises a lens 5, mounted and secured in a lens cover aperture 10a of a lens cover 10. The lens cover 10 may be substantially opaque. The lens cover aperture 10a may have a diameter in the range of 1-50 mm. The lens 5 is located at the center of cross hairs 5.5 (FIG. 1), which are positioned on the exterior surface of the lens cover 10.

The lens cover 10 with lens 5 is connected to a substantially opaque, generally cylindrical, chamber 20. The chamber 20 may be formed of plastic, although other materials may be substituted. The chamber 20 is preferably light tight, and does not admit any significant amount of external ambient light except through an inner wall aperture 30 (FIGS. 4, 6), which is positioned at the center of an inner wall 25 of the chamber 20. The inner wall 25 defines a first chamber section 25a and a second chamber section 25b. A term 'lens-aperture chamber' 40 may be used to identify a portion of the apparatus 4 which includes the lens 5, the lens cover 10, the chamber 20, with the inner wall 25 wherein the inner wall aperture 30 is positioned.

Figure 4:
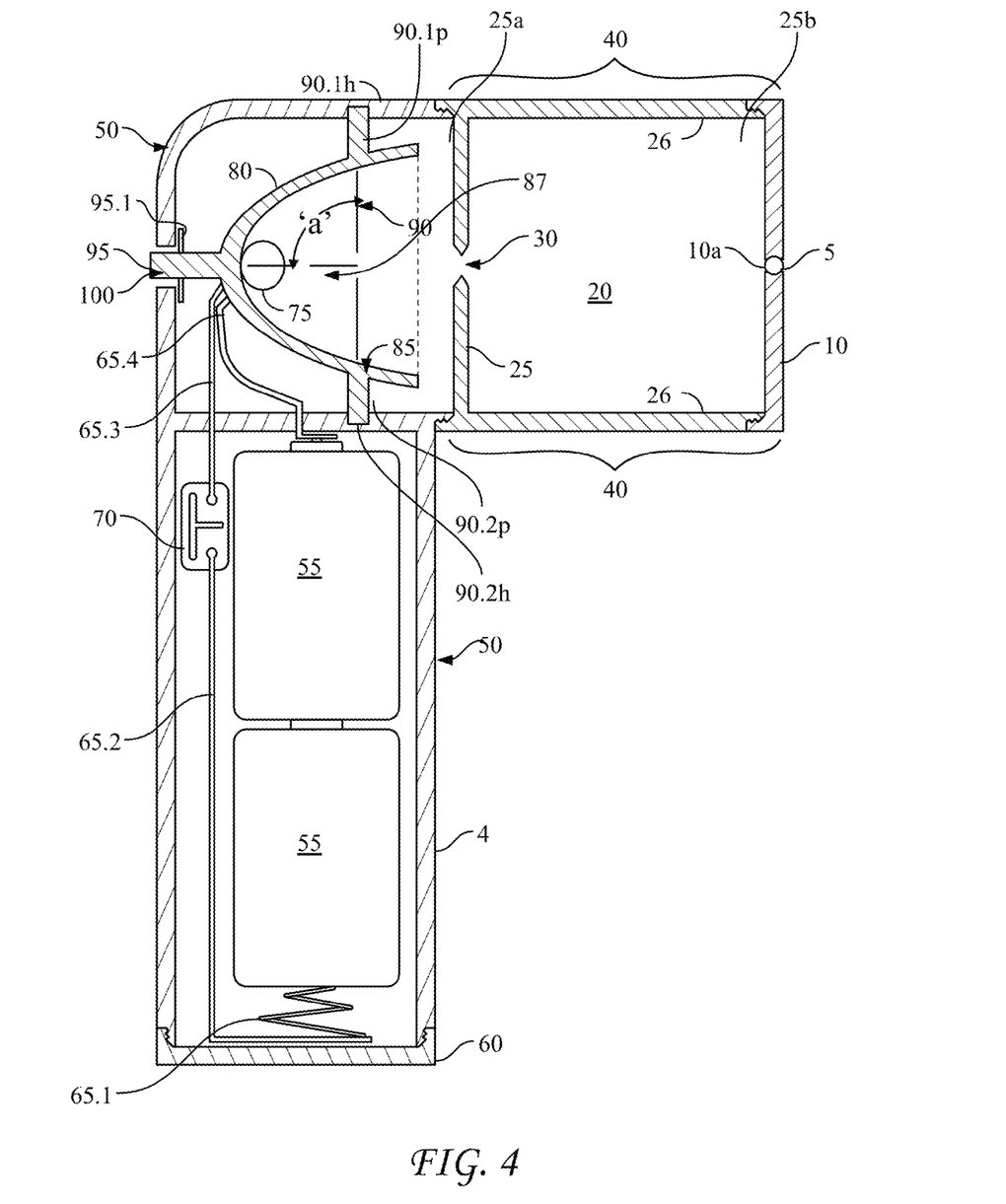
FIG. 4 is a sectional view of the apparatus of FIG. 1.
Figure 5:
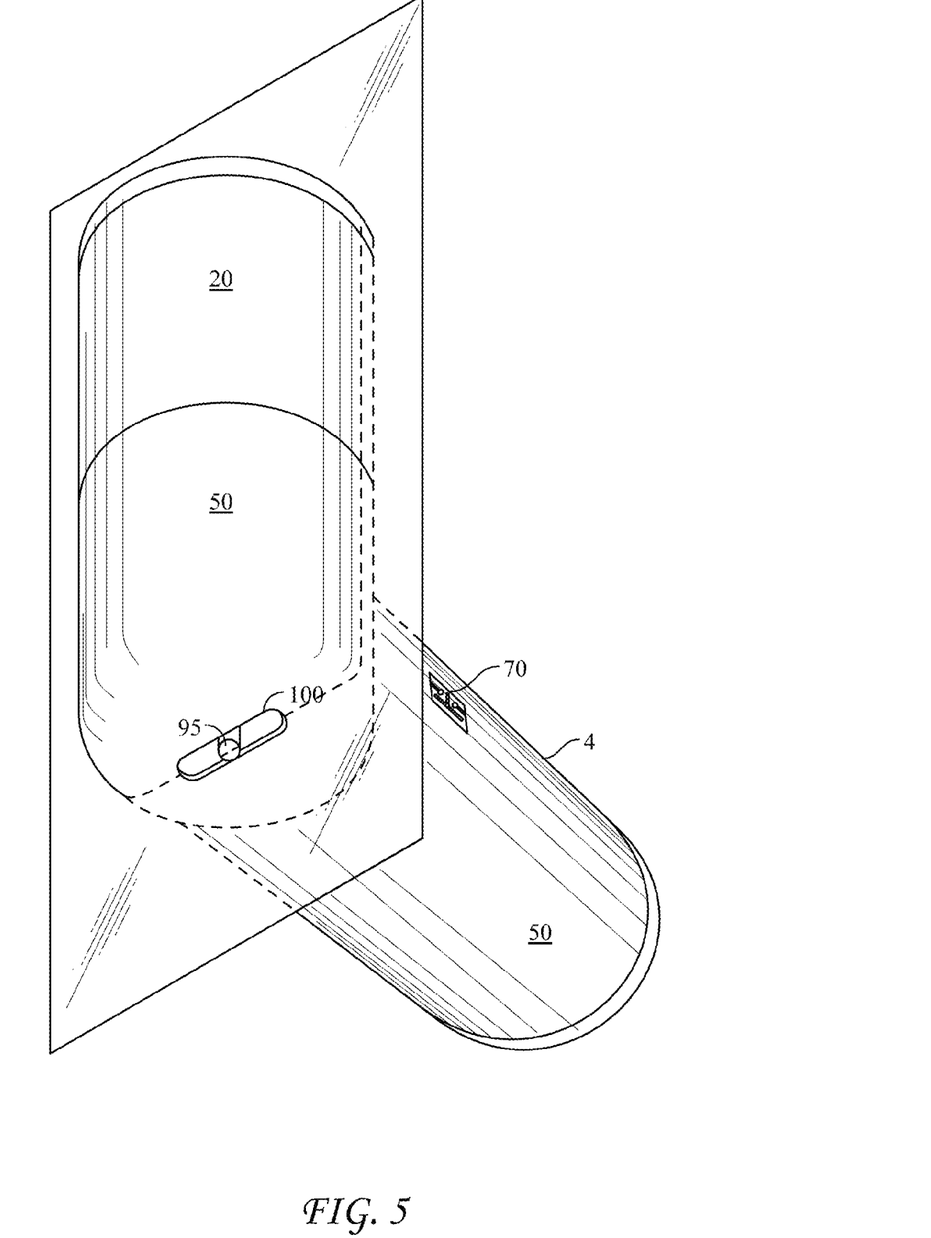
FIG. 5 is a further perspective view of the apparatus of FIG. 1.

Again referring to the apparatus 4 while in its upright position as in FIG. 4, a vertically-oriented portion (when in use) of the apparatus 4 constitutes a chassis 50 which may house a light source 75, such as a conventional incandescent light bulb, an LED array, or the like, in a manner similar to conventional flashlights. The chassis 50 may enclose an electrical power source 55, such as one or more conventional batteries, to provide power to the light source 75. The power source 55 may be accessible through a conventional threshed, detachable base 60. The preferred diameter of the lens cover aperture 10a, discussed above, may be determined based upon the luminosity of the light source 75.

A conventional electrical wiring circuit comprises segments such as a metal spring 65.1 positioned near the base of the apparatus 4 and making contact with the power source 55, a first segment of wiring 65.2 connecting the metal spring 65.1 base to a conventional, externally operable, electrical switch 70, a second segment of wiring 65.3, operably connecting the switch 70 to the light source 75 and a third segment of wiring 65.4 extending from the light source 75 to the power source 55, completing the circuit.

The chassis 50 portion may connect to the lens-aperture chamber 40 at an approximately 90° angle. As is typical of conventional flashlights, the light source 75 may be mounted in a reflector 80, which may be parabolic. The interior surface of the reflector 80 may be coated with a highly reflective mirror surface 85.

Referring again to FIG. 4, the reflector 80 supporting the light source 75 may be flexibly mounted within the chassis 50 of the apparatus 4, permitting the reflector 80, with the light source 75, to pivot as a single structure inside the chassis 50 along a plane 87 defining a neutral orientation of the reflector 80, which plane is defined as being at a 90° angle 'a' to a vertical line of axis 90 which may connect two axially aligned, flexible pivot members 90.1p and 90.2p. Each of the pivot members 90.1p and 90.2p may be appendages of the reflector 80 and may extend away from the reflector 80, one pivot member 90.1p extending above the reflector 80, and one pivot member 90.2p extending below the reflector 80. These pivot members may be secured to the chassis 50 in holes 90.1h and 90.2h of the chassis 50, and which two holes are also axially aligned with the vertical axis 90.

A tab 95 may extend from the reflector 80, and may be positioned on an exterior surface at an apex end of the reflector 80, extending outwardly from the reflector 80 and continuing through a slot 100 on a back exterior surface of the chassis 50. The tab 95 allows an individual to manually pivot the reflector 80 with its highly reflective mirror surface 85 and light source 75 along the horizontal plane 87 within the limits of angle 'b' as defined by the slot 100 as in FIG. 6, being approximately in the range of 20°-90°.

Figure 6:
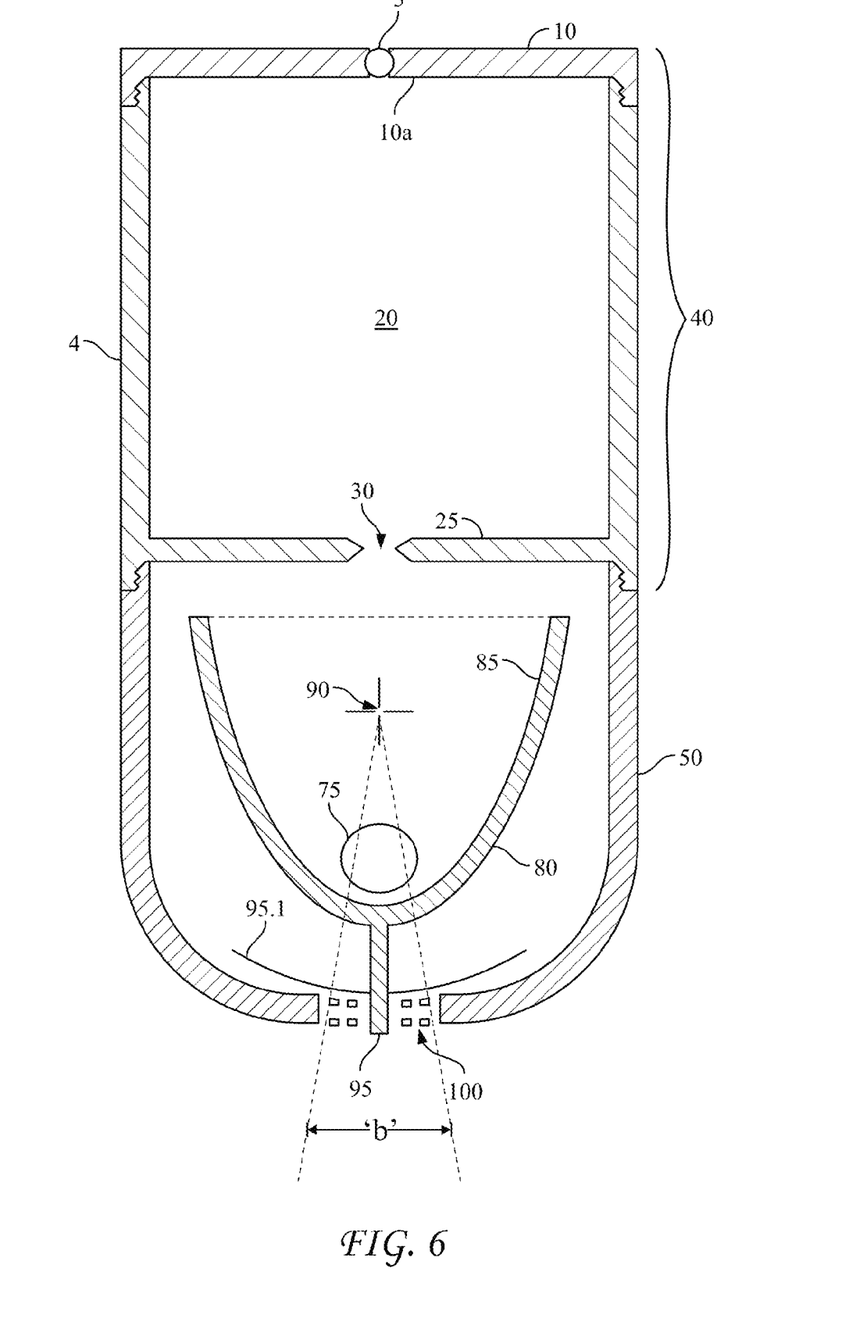
FIG. 6 is a further sectional view of the apparatus of FIG. 1.

A dust/contamination barrier 95.1 may skirt the tab 95 so that while the individual manipulates the tab 95 back and forth within the confines of the slot entering the interior of the apparatus, dust and other contaminants may be prevented from entering the interior of the apparatus 4.

FIG. 7 illustrates perception by an individual 6, through an individual's eye 6a, of a particle 8 displayed on a retina of the individual 6 using only a naked eye.

FIG. 8 illustrates perception by the individual 6, through the individual's eye 6a, utilizing the apparatus 4. Utilizing the apparatus 4 an image 8a of the particle 8 is displayed on the retina of the individual 6.

Referring now to FIGS. 2 and 8, the apparatus 4 is illustrated as utilized by the individual 6 attaching the light source 75 to the chamber 20, turning on the switch 70 and holding the lens 5 close to the eye (between 1/16" and 1"), and looking through the lens 5 directly at the light bulb 75, thereby viewing any microscopic details within the eye.

Figure 13:
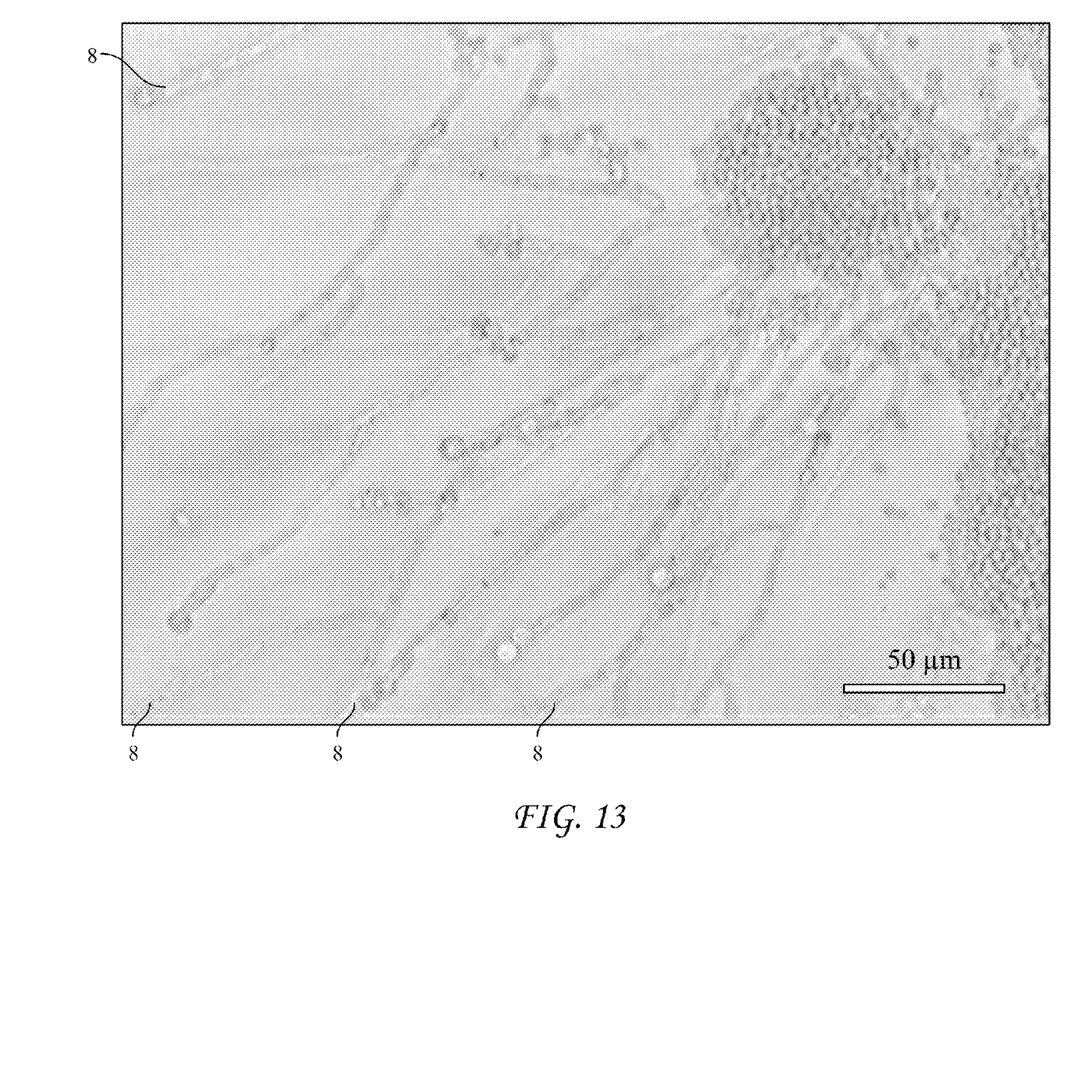
FIG. 13 is an illustration of particles as viewed under a microscope at an approximately 200× magnification.

FIG. 13 illustrates the several of the particles 8 as viewed by a microscope at an approximately 200× magnification. This illustrates what is substantially what may be seen by the individual 6, when the individual 6 views his/her eye utilizing the apparatus 4.

When the apparatus 4 is held in a proper position for viewing, the individual will notice that the wide diameter of the lens cover 10 may cause portions of the circumferential edge of the lens cover 10 to rest against the individual's eyebrow and/or nose and/or cheek as in FIG. 2. This design feature will assist the individual to hold the apparatus steady while looking through the small lens 5. The individual can manipulate the tab 95 within the confines of the slot 100 to change the illumination and the contrast lighting of the vitreous particles which may be observed in situ.

Figure 9:
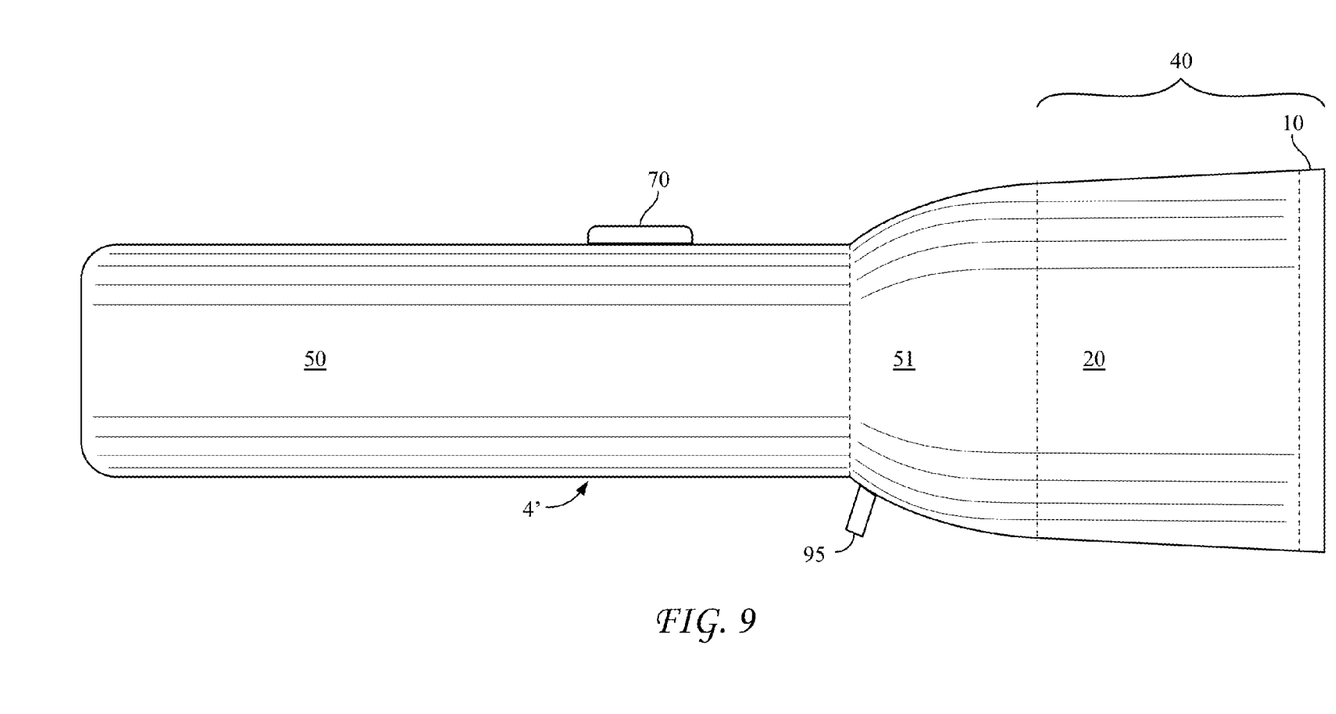
FIG. 9 is a side view of a second embodiment of an apparatus according to the present invention.
Figure 10:
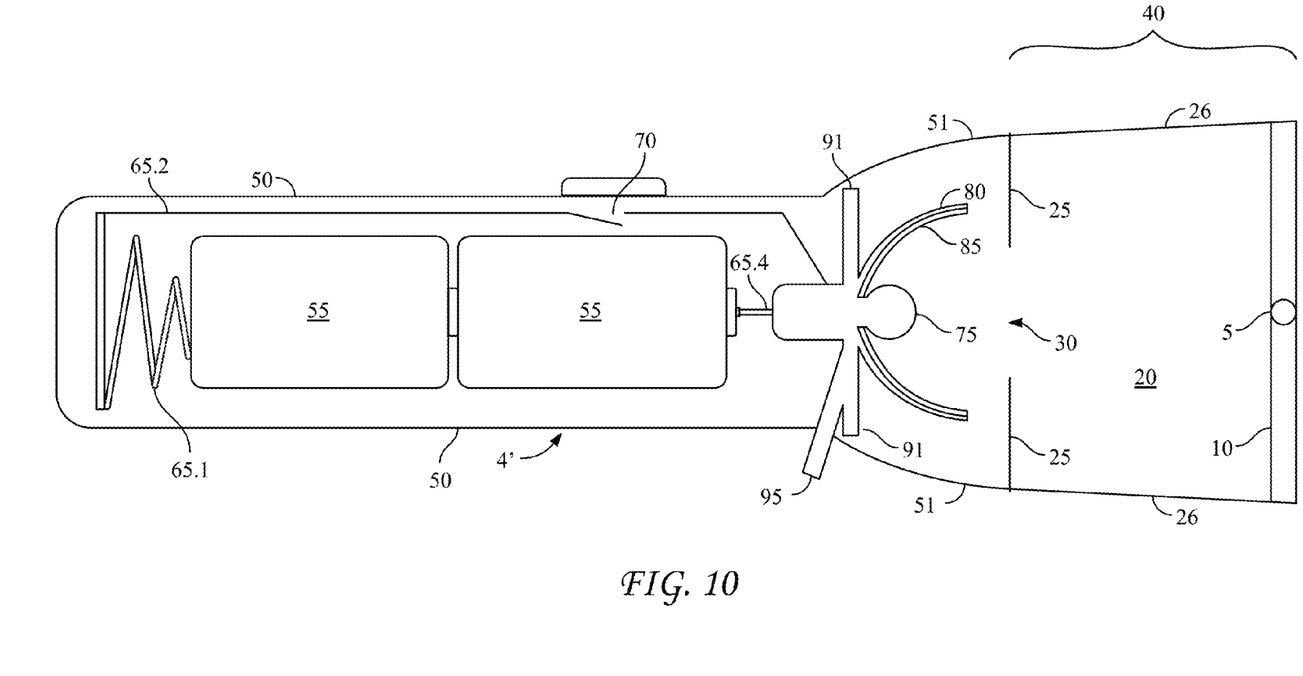
FIG. 10 is a side-sectional view of the embodiment of FIG. 9.
Figure 11:
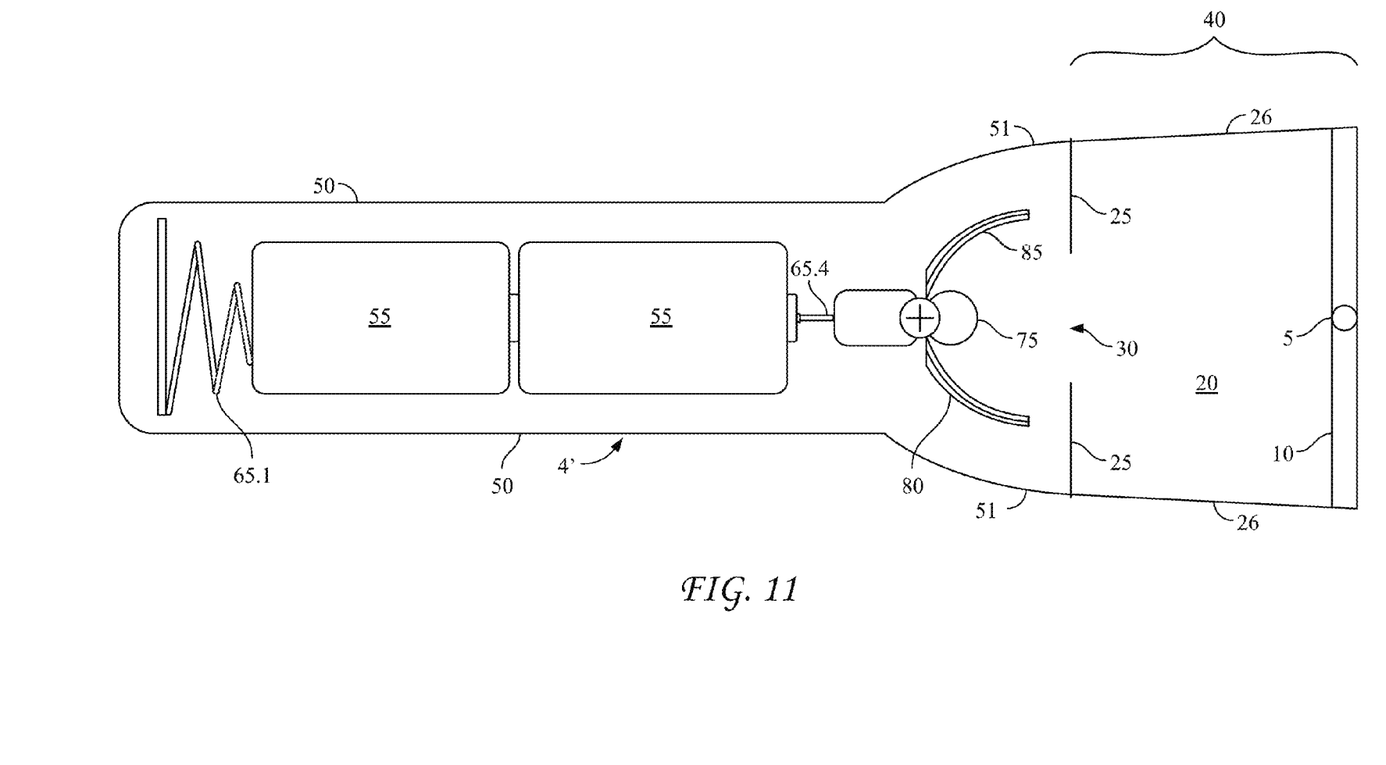
FIG. 11 is a top-sectional view of the embodiment of FIG. 9

FIGS. 9-11 illustrate a second, alternative embodiment of my present invention. The alternative embodiment of the apparatus has been renumbered 4', although other common elements have retained their previous numerical representations.

The apparatus 4' is substantially the same as the apparatus 4. A primary difference is that the chassis 50 extends linearly away from the lens aperture chamber 40, rather than turning at a 90° angle. The apparatus 4' operates, and is utilized, in the same manner as is the apparatus 4 discussed above.

Figure 12:
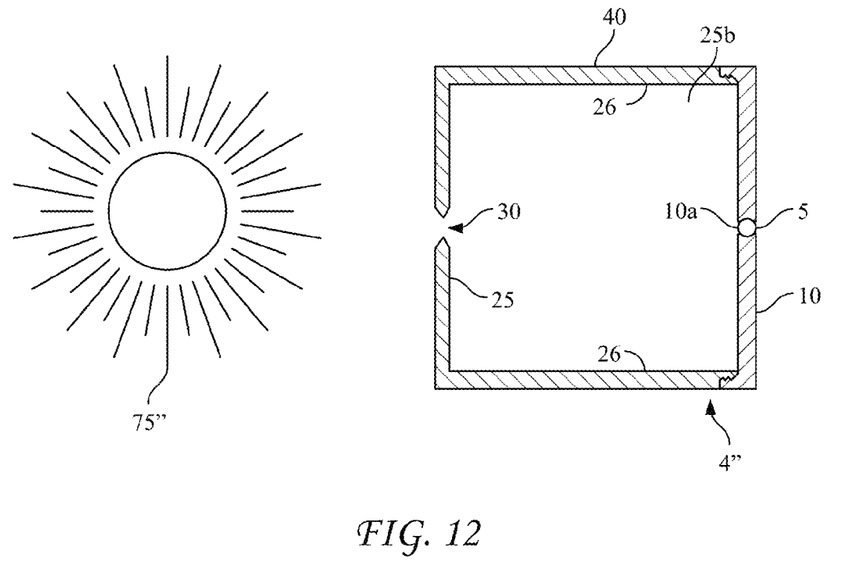
FIG. 12 is a side view of a third, alternative embodiment of the present invention.

FIG. 12 illustrates an apparatus 4" according to a third embodiment of the present invention. The apparatus 4" does not include its own dedicated light source 75, power source 55 or related circuitry. Rather the apparatus 4" relies upon a source ambient light 75", such as an external electrical light source, ambient light from the sun, or the like, to illuminate the particles 8.

From the foregoing it will be observed that numerous variations and modifications may be effected without departing from the spirit and scope of the invention. It is to be understood that no limitation illustrated herein is intended, or inferred. It is, of course, intended to cover by the appended claims all such modifications as fall within the scope of the claims.

What is claimed:

1. An apparatus for permitting self-examination of the interior space of an individual's eye, the apparatus comprising:
   a chassis defining a chamber, the chassis having an inner wall disposed therein, the inner wall defining a first chamber section and a second chamber section, the inner wall further including an inner wall aperture;
   a chamber wall enclosing the first end;
   a reflector flexibly mounted within the first chamber section, the reflector having a neutral orientation directed substantially towards the chamber wall, the reflector further including a tab for deflecting the reflector away from the neutral position of the reflector;
   a lens cover enclosing the second chamber section, the lens cover including a lens cover aperture disposed in the lens cover and a lens disposed in the lens cover aperture; and
   a light source disposed within the reflector, wherein the reflector and light source are adapted to direct light through the inner wall aperture and the lens, wherein the lens cover is adapted for placement proximate the individual's eye, such that light from the light source is emitted into the individuals eye, permitting the individual to examine the interior space of the individual's eye.

2. The apparatus of claim 1 wherein the chamber is substantially opaque.

3. The apparatus of claim 1 wherein the lens is substantially spherical.

4. The apparatus of claim 3 wherein the lens has a diameter in the range of 1 mm to 10 mm.

5. The apparatus of claim 1 wherein the lens is substantially hemispherical.

6. The apparatus of claim 5 wherein the lens has a diameter in the range of 1 mm to 10 mm.

7. The apparatus of claim 1 wherein the reflector is flexibly mounted within the first chamber section by a flexible pivot member extending between the reflector and the chassis.

8. The apparatus of claim 1 wherein the reflector is flexibly mounted within the first chamber section by a plurality of flexible pivot members extending between the reflector and the chassis.

9. The apparatus of claim 1 including a power source coupled to the light source to provide power to illuminate the light source.

10. The apparatus of claim 9 including a switch operably connecting the power source to the light source.

11. A method for permitting an individual to self-examine the interior space of the individuals eye for the presence of a particle within the eye, the method comprising:
    providing an apparatus as claimed in claim 1;
    holding the lens of the apparatus spaced from the individual's eye;
    viewing through the lens toward the light source to illuminate the interior of the individual's eye; and
    examining the illuminated interior of the individual's eye while manipulating the tabbed appendage to deflect the reflector and thereby change the background lighting and contrast lighting of the interior of the individual's eye, thereby viewing any such particle within the eye.

12. The method of claim 11, wherein the particle comprises residual piece of organic detritus matter.

13. The method of claim 11, wherein the particle comprises a microorganism.

14. The method of claim 11, wherein the microorganism comprises *Candida*.

15. The method of claim 11 including:
    providing images of potential particles within an eye; and
    comparing the provided images with the viewed particle to determine the type of particle within the eye.

16. The method of claim 11, wherein the lens is held from the individual's eye a distance in the range of 1/16 inch to 1 inch.

17. A method for permitting an individual to self-examine the interior space of the individuals eye for the presence of a particle within the eye, the method comprising:

providing an apparatus comprising a chassis defining a chamber having a first chamber end and a second chamber end, the chassis having an aperture wall substantially enclosing the first chamber end, the aperture wall including an aperture, the chassis further including a lens cover enclosing the second chamber section, the lens cover including a lens cover aperture disposed in the lens cover and a lens disposed in the lens cover aperture;

holding the apparatus at an orientation such that the lens is spaced from the individual's eye;

viewing through the lens toward an ambient source of light to illuminate the interior of the individual's eye; and examining the illuminated interior of the individual's eye while manipulating the orientation of the chassis relative to the individual's eye, thereby viewing any such particle within the eye.

18. The method of claim 17, wherein the particle comprises residual piece of organic detritus matter.

19. The method of claim 17, wherein the particle comprises a microorganism.

20. The method of claim 17, wherein the microorganism comprises *Candida*.

21. The method of claim 17 including:

providing images of potential particles within an eye; and comparing the provided images with the viewed particle to determine the type of particle within the eye.

\* \* \* \* \*